(12) United States Patent
Ortiz et al.

(10) Patent No.: US 9,349,297 B1
(45) Date of Patent: May 24, 2016

(54) SYSTEM AND METHOD FOR NUTRITION ANALYSIS USING FOOD IMAGE RECOGNITION

(71) Applicant: Fitly Inc., Philadelphia, PA (US)

(72) Inventors: Caonabo Anthony Ortiz, Philadelphia, PA (US); Domingo Mery, Santiago (CL)

(73) Assignee: Fitly Inc., Philadelphia, PA (US)

( * ) Notice: Subject to any disclaimer, the term of this patent is extended or adjusted under 35 U.S.C. 154(b) by 0 days.

(21) Appl. No.: 14/848,992

(22) Filed: Sep. 9, 2015

(51) Int. Cl.
| | |
|---|---|
| *G09B 19/00* | (2006.01) |
| *G09B 5/00* | (2006.01) |
| *H04N 7/18* | (2006.01) |
| *G06T 7/00* | (2006.01) |
| *G06K 9/46* | (2006.01) |
| *G06K 9/62* | (2006.01) |
| *G06T 5/00* | (2006.01) |
| *G06T 7/60* | (2006.01) |
| *G06K 9/52* | (2006.01) |
| *G06T 7/40* | (2006.01) |

(52) U.S. Cl.
CPC ............... *G09B 5/00* (2013.01); *G06K 9/4604* (2013.01); *G06K 9/4652* (2013.01); *G06K 9/52* (2013.01); *G06K 9/6201* (2013.01); *G06T 5/006* (2013.01); *G06T 7/0042* (2013.01); *G06T 7/0083* (2013.01); *G06T 7/0085* (2013.01); *G06T 7/408* (2013.01); *G06T 7/60* (2013.01); *G09B 19/0092* (2013.01); *H04N 7/18* (2013.01); *G06K 2009/4666* (2013.01); *G06T 2207/20144* (2013.01)

(58) Field of Classification Search
CPC .... G09B 5/00; G09B 19/0092; G06K 9/4604; G06K 9/52; G06K 9/6201; G06K 9/4652; G06T 7/60; G06T 7/408; G06T 5/006; G06T 7/0042; G06T 7/0083; H04N 7/18

USPC .......................................................... 434/127
See application file for complete search history.

(56) References Cited

U.S. PATENT DOCUMENTS

| | | | | |
|---|---|---|---|---|
| 5,793,879 | A * | 8/1998 | Benn | A22B 5/007 348/89 |
| 5,815,198 | A * | 9/1998 | Vachtsevanos | G01N 21/88 348/125 |
| 5,818,953 | A * | 10/1998 | Queisser | G01N 21/88 209/580 |
| 6,457,250 | B1 | 10/2002 | Mingus et al. | |
| 6,508,762 | B2 * | 1/2003 | Karnieli | G06F 19/324 128/921 |
| 7,860,277 | B2 * | 12/2010 | Mulder | B07C 5/3422 382/110 |
| 8,345,930 | B2 | 1/2013 | Tamrakar et al. | |
| 8,363,913 | B2 * | 1/2013 | Boushey | A23L 1/293 128/921 |
| 8,439,683 | B2 | 5/2013 | Puri et al. | |
| 8,605,952 | B2 | 12/2013 | Boushey et al. | |
| 8,625,889 | B2 | 1/2014 | De Oliveira et al. | |
| 2002/0022774 | A1 * | 2/2002 | Karnieli | G06F 19/324 600/300 |
| 2002/0027164 | A1 * | 3/2002 | Mault | A61B 5/1118 235/462.46 |

(Continued)

*Primary Examiner* — Michael Grant
(74) *Attorney, Agent, or Firm* — Beacon Patent Intelligence LLC; Eugene H. Nahm

(57) ABSTRACT

The present disclosure provides a system and method for determining a nutritional value of a food item. The system and method utilizes a food container as a model to adjust various types of distortions that exists in an instant image of the food container that retains the food item. The instant image may be compared to the model image of the food container to correct any distortions. The food container includes a boundary which has a predetermined color. The predetermined color of the boundary can be used to adjust the color configuration of the instant image, thereby increasing the accuracy of the food identification.

20 Claims, 11 Drawing Sheets

(56) References Cited

U.S. PATENT DOCUMENTS

| | | | |
|---|---|---|---|
| 2002/0047867 A1* | 4/2002 | Mault | A61B 5/1118 715/810 |
| 2002/0118360 A1* | 8/2002 | Shultz | G01N 21/9045 356/239.4 |
| 2003/0076983 A1* | 4/2003 | Cox | G06F 19/3475 382/110 |
| 2003/0181795 A1* | 9/2003 | Suzuki | A61B 5/0002 600/300 |
| 2007/0007279 A1* | 1/2007 | Chun | H05B 6/6441 219/506 |
| 2007/0030339 A1* | 2/2007 | Findlay | G06Q 10/10 348/14.01 |
| 2008/0306770 A1* | 12/2008 | Sysko | G06F 19/3437 705/3 |
| 2008/0306924 A1* | 12/2008 | Paolini | G06F 17/30026 |
| 2009/0012433 A1* | 1/2009 | Fernstrom | A61B 5/1112 600/593 |
| 2010/0047745 A1* | 2/2010 | Bergqwist | A61B 5/14532 434/127 |
| 2010/0080875 A1* | 4/2010 | Miller-Kovach | G06F 19/3475 426/232 |
| 2010/0173269 A1* | 7/2010 | Puri | G09B 19/0092 434/127 |
| 2010/0191155 A1* | 7/2010 | Kim | A61B 5/1118 600/595 |
| 2010/0199232 A1* | 8/2010 | Mistry | G06F 1/163 715/863 |
| 2010/0249530 A1* | 9/2010 | Rankers | G06F 19/3456 600/300 |
| 2010/0262554 A1* | 10/2010 | Elliott | G01C 21/20 705/323 |
| 2011/0050880 A1* | 3/2011 | Bourg, Jr. | G01N 21/8851 348/89 |
| 2011/0182477 A1* | 7/2011 | Tamrakar | G06T 7/0002 382/110 |
| 2011/0243392 A1* | 10/2011 | Miyahara | G06Q 30/02 382/110 |
| 2011/0268311 A1* | 11/2011 | Hudnut | A47J 37/00 382/100 |
| 2012/0096405 A1* | 4/2012 | Seo | G06F 3/04886 715/825 |
| 2012/0135384 A1* | 5/2012 | Nakao | G09B 19/0092 434/127 |
| 2012/0170801 A1* | 7/2012 | De Oliveira | G06K 9/6256 382/103 |
| 2012/0171646 A1* | 7/2012 | Chen | G09B 19/0092 434/127 |
| 2012/0179665 A1* | 7/2012 | Baarman | G06F 19/3475 707/709 |
| 2012/0229624 A1* | 9/2012 | Calman | G06F 19/3456 348/135 |
| 2013/0004923 A1* | 1/2013 | Utter, II | G06F 19/3475 434/127 |
| 2013/0027424 A1* | 1/2013 | Mochizuki | G06F 19/3475 345/620 |
| 2013/0045467 A1* | 2/2013 | Kamen | A61M 5/14244 434/127 |
| 2013/0058566 A1* | 3/2013 | Sato | G06K 9/4642 382/159 |
| 2013/0085345 A1* | 4/2013 | Geisner | G06Q 30/00 600/300 |
| 2013/0113933 A1* | 5/2013 | Boushey | A23L 1/293 348/143 |
| 2013/0157232 A1* | 6/2013 | Ehrenkranz | G01G 19/4146 434/127 |
| 2013/0170714 A1* | 7/2013 | Aizawa | G06K 9/00624 382/110 |
| 2013/0203024 A1* | 8/2013 | Dekar | B25J 11/008 434/127 |
| 2014/0078152 A1* | 3/2014 | Chang | G06T 7/0083 345/441 |
| 2016/0012749 A1* | 1/2016 | Connor | A61B 5/11 600/13 |

* cited by examiner

SYSTEM AND METHOD FOR NUTRITION ANALYSIS USING FOOD IMAGE RECOGNITION

BACKGROUND

1. Field of the Invention

The subject matter described herein relates generally to diet management and nutrition analysis. More specifically, the present disclosure is related to computer vision techniques of food recognition based on an image of the food and the food container.

2. Description of Related Art

The lack of accurate weight information in nutrition analysis and inaccuracy of food recognition can lead to inefficient diet management. Currently, there exist some handheld applications and computer vision systems that capture food images for nutritional value analysis. Due to many varying factors, such as lack of a predefined container, lighting, focal length, which exists in the conventional food image recognition methods, the accuracy of the nutrition analysis is very low. One of the reasons these existing image recognition technologies performs poorly when assessing accurate nutrition data is largely due to their inability to capture volume, density, and/or weight of the food from just a single image of the food. Volume, density, and weight are difficult to gauge without a predefined container included in the image. There are currently no solutions that provide accurate identification and weight information of a food item due to the absence of a fixed and predefined container which is needed for reference. Moreover, there are no solutions currently available to provide accurate identification and weight information from the combination of a fixed and predefined container that has a load sensor to communicate the exact weight of the food item.

Many research studies have recently shown clear correlations between poor dieting and health conditions. Poor diets, such as overeating, under eating, and/or consuming poor quality foods have been linked to certain medical conditions like diabetes, cancer, heart disease, hypertension, chronic kidney disease, obesity, and the like. For consumers and patients trying to control the quality and habit of consuming food, it is often difficult to identify what kinds of food they are consuming and to improve their eating habits and health conditions. It is cumbersome for the consumers to meet their prescribed nutritional requirements or dietary regimen necessary each time they prepare a meal.

Therefore, there is a need for a system and method that accurately recognizes the type of food being consumed and the weight of the food, in order to be aware of the nutrition and calories being consumed at each meal. In addition, there also is a need for an accurate computer vision technique system and method that can identify the food being consumed at each meal.

SUMMARY

The subject matter of this application may involve, in some cases, interrelated products, alternative solutions to a particular problem, and/or a plurality of different uses of a single system or article.

In one aspect, a system using a food recognition device in communication with a database via a network that determines a nutritional value of a food item is provided. The system may comprise a food container, a weight sensor, an image capturing device, and a food recognition device. The food container may be formed with one or more partitions therein. The one or more partitions may be defined by a boundary outlining a divider and a peripheral wall formed by the food container. The boundary may have a predetermined color that is dissimilar from other surfaces of the food container. Further, the food container may receive the food item and retain it.

The weight sensor may be placed within the food container, and positioned to measure a weight of the food item being received by each of the one or more partitions. The image capturing device may capture an image of the food container. The food recognition device may be in communication with the weight sensor and the image capturing device.

The food recognition device may obtain the image of the food container from the image capturing device. The food recognition device may further correct the orientation of the image by aligning the boundary in the image with the boundary in a reference food container image stored in the database. In addition, the food recognition device may adjust the color of the image based on the predetermined color of the boundary. The image may be segmented based on the boundary to isolate each of the one or more partitions by the food recognition device. Lastly, the food recognition device may identify a type of the food item by comparing each segmented image to a reference segmented food image stored in the database. The present disclosure provides that the database is on the food container, the food recognition device, and/or a server via the network.

In another aspect, a method to use a system using a food recognition device is provided. The system may be in communication with a database via a network, and determines a nutritional value of a food item. The method may comprise the following steps.

The method may begin with the image capturing device capturing an image of a food container. The food container may have one or more partitions, where the one or more partitions is defined by a boundary outlining a divider and a peripheral wall formed by the food container. The boundary may have a predetermined color that is dissimilar from other surfaces of the food container. Further, the food container may receive the food item and retain it.

The method may continue with a food recognition device obtaining the image of the food container from the image capturing device. The image capturing device may be in communication with the food recognition device. The food recognition device may further obtain a weight of the food item from a weight sensor, where the weight sensor may be positioned to measure the weight of the food item being received by each of the one or more partitions. The weight sensor may be in communication with the food recognition device.

The food recognition device may further correct the orientation of the image by aligning the boundary in the image with the boundary in a reference food container image stored in the database. The method may further comprise adjusting the color of the image based on the predetermined color of the boundary and segmenting the image based on the boundary to isolate each of the one or more partitions. Finally, the food recognition device may identify the type of the food item by comparing each segmented image to a reference segmented food image stored in the database.

DETAILED DESCRIPTION

Figure 1:
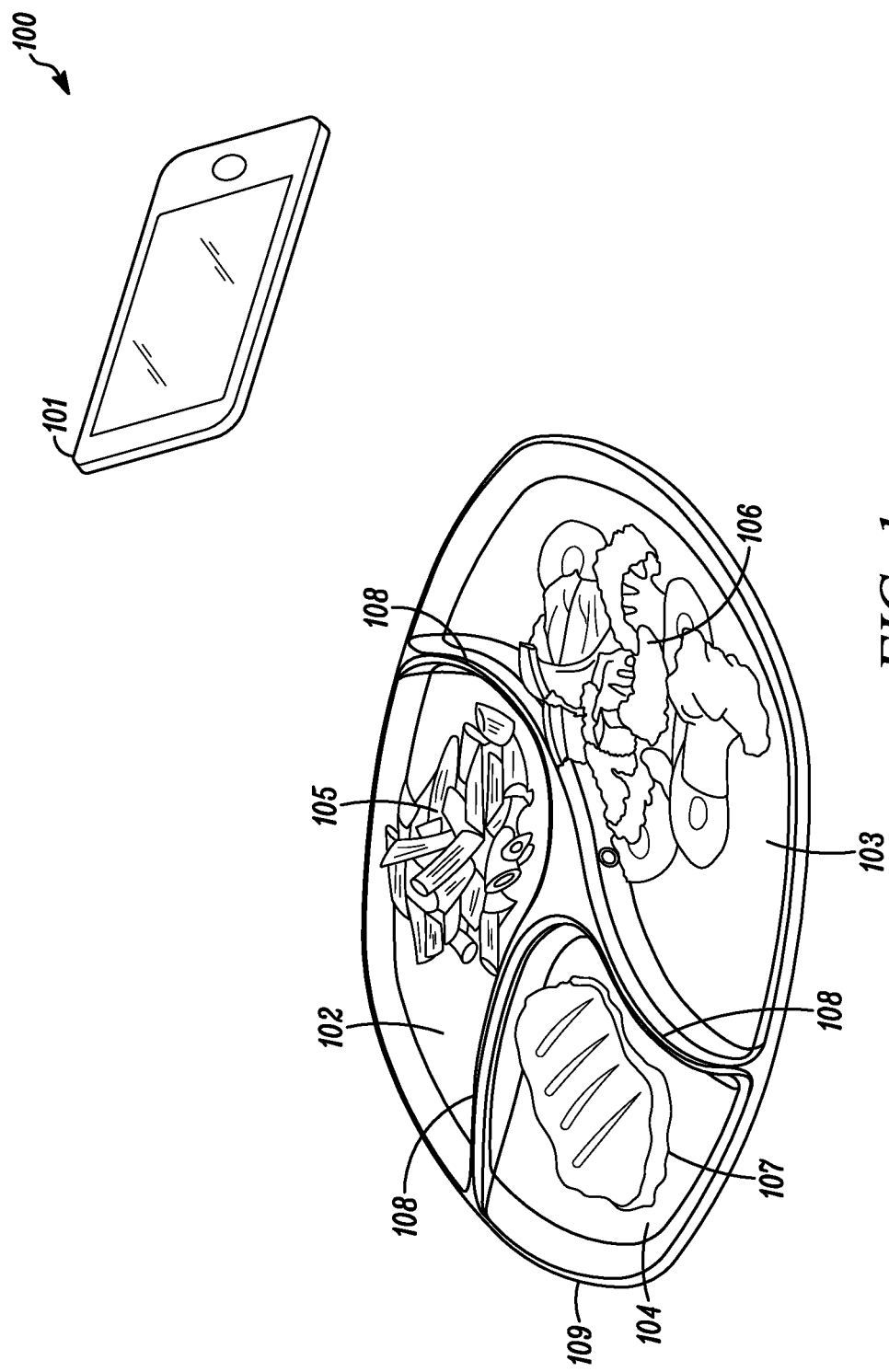
FIG. 1 provides an exemplary embodiment of the food recognition device and the food container in use.

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

In referring to the description, specific details are set forth in order to provide a thorough understanding of the examples disclosed. In other instances, well-known methods, procedures, components, and materials have not been described in detail as not to unnecessarily lengthen the present disclosure.

It should be understood that if an element or part is referred herein as being "on", "against", "in communication with", "connected to", "attached to", or "coupled to" another element or part, then it can be directly on, against, in communication with, connected, attached or coupled to the other element or part, or intervening elements or parts may be present. When used, the term "and/or", includes any and all combinations of one or more of the associated listed items, if so provided.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

Various operations may be described as multiple discrete operations in turn, in a manner that may be helpful in understanding embodiments; however, the order of description should not be construed to imply that these operations are order dependent.

Spatially relative terms, such as "under" "beneath", "below", "lower", "above", "upper", "proximal", "distal", and the like, may be used herein for ease of description and/or illustration to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable. Such descriptions are merely used to facilitate the discussion and are not intended to restrict the application of disclosed embodiments.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

Some embodiments of the present invention may be practiced on a computer system that includes, in general, one or a plurality of processors for processing information and instructions, RAM, for storing information and instructions, ROM, for storing static information and instructions, a database such as a magnetic or optical disk and disk drive for storing information and instructions, modules as software units executing on a processor, an optional user output device such as a display screen device (e.g., a monitor) for display screening information to the computer user, and an optional user input device.

As will be appreciated by those skilled in the art, the present examples may be embodied, at least in part, a computer program product embodied in any tangible medium of expression having computer-usable program code stored therein. For example, some embodiments described below with reference to flowchart illustrations and/or block diagrams of methods, apparatus (systems) and computer program products can be implemented by computer program instructions. The computer program instructions may be stored in computer-readable media that can direct a computer or other programmable data processing apparatus to function in a particular manner, such that the instructions stored in the computer-readable media constitute an article of manufacture including instructions and processes which implement the function/act/step specified in the flowchart and/or block diagram. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

Generally, the present invention concerns a system for determining a nutritional value of a food item based on a food recognition process. The present invention utilizes a predefined food container as a model reference, in connection with a weight sensor for weight measurement of the food item placed in the food container. An image of the food container with the food contained therein may be captured. The image includes the predefined food container, which provides a reference to predefined values, such as color, shape, orientation, size, lighting, and the like. The image may be transformed to match the predefined reference values derived from the reference food container, which corrects perspective distortion, color saturation, lighting, sizing, and orientation. The dividers of the container can be used to segment the partitions of the container, resulting in the individual identification of each food item retained by each of the partitions of the food container. The predefined reference food container improves the accuracy of food identification by providing accurate image data of the food item derived from the reference food container's predefined reference values.

The food recognition method of the present disclosure involves computer vision technique. The food container of the present invention may have certain identifiable structural and/or visual properties that can be provided as references when processing an image of the food container having the food item placed therein. The food container may have structural and visual properties, such as dividers, partitions, boundaries, color, and patterns. By involving the food container as a model reference, processing of the food image can be streamlined to provide a more accurate identification of the type of the food. The computer vision technique method which involves the food container may comprise image rectification, image segmentation, and food identification steps that are based on the known structural and/or visual properties of the model food container.

The system for determining a nutritional value of a food item based on a food recognition process may comprise one or more computers or computerized elements, in communication with one another, working together to carry out the different functions of the system. The invention contemplated herein may further comprise a non-transitory computer readable media configured to instruct a computer or computers to carry out the steps and functions of the system and method, as described herein. In some embodiments, the communication among the one or more computer or the one or more processors alike, may support a plurality of encryption/decryption methods and mechanisms of various types of data.

The system may comprise a computerized user interface provided in one or more computing devices in networked communication with each other. The computer or computers of the computerized user interface contemplated herein may comprise a memory, processor, and input/output system. In some embodiments, the computer may further comprise a networked connection and/or a display screen. These computerized elements may work together within a network to provide functionality to the computerized user interface. The computerized user interface may be any type of computerized interfaces known in the art capable of allowing a user to input data and receive a feedback therefrom. The computerized user interface may further provide outputs executed by the system contemplated herein.

Database and data contemplated herein may be in the format including, but are not limiting to, XML, JSON, CSV, binary, over any connection type: serial, Ethernet, etc. over any protocol: UDP, TCP, and the like.

Computer or computing device contemplated herein may include, but are not limited to, virtual systems, Cloud/remote systems, desktop computers, laptop computers, tablet computers, handheld computers, smartphones and other cellular phones, and similar internet enabled mobile devices, digital cameras, a customized computing device configured to specifically carry out the methods contemplated in this disclosure, and the like.

Network contemplated herein may include, for example, one or more of the Internet, Wide Area Networks (WANs), Local Area Networks (LANs), analog or digital wired and wireless telephone networks (e.g., a PSTN, Integrated Services Digital Network (ISDN), a cellular network, and Digital Subscriber Line (xDSL)), radio, television, cable, satellite, and/or any other delivery or tunneling mechanism for carrying data. Network may include multiple networks or subnetworks, each of which may include, for example, a wired or wireless data pathway. The network may include a circuit-switched voice network, a packet-switched data network, or any other network able to carry electronic communications. Examples include, but are not limited to, Picture Transfer Protocol (PTP) over Internet Protocol (IP), IP over Bluetooth, IP over WiFi, and PTP over IP networks (PTP/IP).

Weight sensors contemplated herein may measure weight of the food item in various ways which may include, but are not limited to, electrically resistive strain gauges, force sensitive resistors, photoelectric weight sensors, hydraulic weight sensors, pneumatic weight sensors, and the like.

Image capturing devices contemplated herein may include, but are not limited to, various types of cameras, such as, DSLR, non-SLR digital cameras (e.g., but not limited to, compact digicams and SLR-like bridge digital cameras (also known as advanced digital cameras), and SLR-like interchangeable lens digital cameras), as well as video recorders (e.g., but not limited to, camcorders, analog cameras and IP cameras, and the like; a device that can provide a video feed of any duration, such as a DVR; a portable computing device having a camera, such as a tablet computer, laptop computer, smartphones); and the like.

The image files contemplated herein may be any digital image format capable of being interpreted by a computer or computing device. Examples of image files contemplated herein include, but are not limited to JPEG, GIF, TIFF, PNG, Bitmap, RAW, PNM, WEBP, and the like.

System and method for determining a nutritional value of a food item is provided. The system may comprise a food container, a weight sensor, an image capturing device, a database, and a food recognition device. The components of the system may be in communication with one another in a networked system environment. The food container may comprise one or more processors and a memory and enabled to be in an electronic communication with the components of the system. Each of these components of the system may further be equipped with various types of transceivers and/or other communication devices, in order to receive and send data to one another.

The food container may form one or more partitions, where each of the one or more partitions receives and/or retain a food item thereon to be consumed by a user. The one or more partitions may be defined by a boundary outlining the one or more partitions of the food container. The one or more partitions may be compartmentalized by a divider and a peripheral wall formed by the food container. The one or more partitions may be repositionable to adjust the configuration and/or size of each of the one or more partitions.

The food container may have predetermined structural properties, such that in the process of food identification and nutritional value determination, the predetermined structural properties may be used as a structural model/reference. The utilization of the food container's structural properties will be further discussed in the following descriptions.

In one embodiment, the food container may have a predetermined arrangement of the one or more partitions defined by the boundary. The one or more partitions may be arranged and designed in a certain way to be provided as a structural model. As such, the arrangement of the one or more partitions and their design may be further utilized in food recognition and computer vision technique. For example, the food container may be a plate having three partitions formed therein. Each of the three partitions may be different in size and shape arranged in order of their sizes in a clockwise direction. This known arrangement orientation may be utilized in computer vision technique and food recognition method described herein.

In another embodiment, the food container may further be assigned with predetermined structural properties, such as shape, orientation, design, size, dimension, weight and the like. These and other structural properties of the food container would be apparent to those having ordinary skill in the art.

In yet another embodiment, the predetermined structural properties of the food container may include visual properties such as color. The food container may have one or more colors defining the one or more partitions and other surfaces of the food container. The body of the food container and the divider may have predetermined colors. In some embodiments, the boundary may have a predetermined color discernibly outlining the one or more partitions of the food container. The predetermined color may be assigned a color value, such as an RGB (Red Green Blue) value. The predetermined color of the boundary may be dissimilar from the other surfaces of the food container, such that the boundary is graphically contrasting or apparent from the surrounding surfaces of the one or more partitions. The boundary's predetermined color may clearly outline and define the one or more partitions, such that the boundary does not graphically blend in with the other surfaces of the food container. As such, the boundary, which may outline the peripheral wall and the divider of the food container, may be discernibly visible in an image of the food container.

In some embodiments, the boundary may be outlined with various line patterns (for example, dashed line, dotted line, etc.) or other visually distinctive patterns. Similar to the predetermined color of the boundary, these line patterns may clearly distinguish the boundary from the other surfaces of the food container.

In some embodiments, the boundary may have a similar and/or the same color as the other surfaces of the food container. The boundary may be one of the predetermined structural properties to be used as a reference. The predetermined structural properties of the food container may include any combination of the boundary's location, size, orientation, shape, and the like.

The food items may be in any form including, but not limited to, liquid, solid, powder, gas, and the like.

The food container may house a plurality of weight sensors. Each of the plurality of weight sensors may be respectively positioned to measure the weight of the food item being retained and received by each of the one or more partitions formed by the food container. The plurality of weight sensors may be in electronic communication with one or more processors, such as the food recognition device, via a network. A weight measured by each of the plurality of weight sensors may be transmitted to the one or more processors of the food recognition device for further evaluation and processing of the food item, according to the present disclosure.

In some embodiments, the food container may house a single weight sensor measuring the weight of the food item being placed in the one or more of partitions. The food items being retained by each of the one or more partitions may be weighed by the single weight sensor accumulatively. Similarly, the food container may comprise a single partition and a single weight sensor to measure the weight of the food item being retained by the single partition.

In some embodiments, the plurality of weight sensors may be repositioned as the configuration of the plurality of partitions are rearranged.

In some embodiments, weights measured from the plurality of weight sensors may be combined to identify a total weight of the food items retained by the one or more partitions.

Each of the one or more partitions may be modular. In some embodiments, the food container may comprise a base and the one or more partitions detachably assembled. Each of the one or more partitions may be detachably fitted to the base. In this embodiment, each of the one or more partitions may be individually designed in various shapes and designs to be interchangeable. The one or more partitions may also be a single unit that may be detachably fitted to the base. This unit may contain various number of partitions, designs, and shapes. The base may comprise the weight sensor and any other components of the food container described herein.

In some embodiments, the food container of the system for determining the nutritional value of a food item may be microwave safe and/or dishwasher safe. In some embodiments, the base which may contain the weight sensor and any other electronic components of the food container may be detached from the one or more partitions. The modular feature of the one or more partitions may be utilized to allow the food container to be used in a microwave and/or a dishwasher. The one or more partitions may then be used in a microwave and/or a dishwasher.

The system may further comprise an image capturing device taking an image of the food container containing the food item(s). The image taken by the image capturing device may be analyzed by the food recognition device to identify a type of the food item being retained by the one or more partitions. The image obtained by the image capturing device may be communicated to the one or more processors of the food recognition device to determine the type of food item being retained by the one or more partitions.

In some embodiments, the image capturing device may be implemented as a standalone and dedicated device, including hardware and installed software, where the hardware is closely matched to the requirements and/or functionality of the software.

In some embodiments, the image capturing device may be installed on or integrated with the food recognition device. There may be multiple image capturing devices each of which positioned to take an image of each of the food items placed in the one or more partitions.

The system for determining a nutritional value of a food item may further comprise a surface sensor. The surface sensor may be positioned to analyze the composition of the food item being retained by the one or more partitions. The surface sensor may identify the composition of the food item in various ways. By way of example, the surface sensor may be a Surface Plasmon Resonance (SPR). The SPR may identify the type of the food item, the preparation status of the food item, and any additional cooking ingredients of the food item. By way of another example, the surface sensor may be a spectrometer capable of detecting pesticide, allergen, chemical compositions, pathogen, and the like from the surface of the food. The spectrometer may identify the type, the preparation status, and the additional cooking ingredients of the food item by analyzing the spectrum. Based on the composition of the food item, the one or more processor may identify the type, the preparation status, and the additional cooking ingredients of the food item. In some embodiments, the surface sensor may be installed on or integrated with the food recognition device.

In a further embodiment, the system may further comprise a temperature measuring device that detects the temperature of the food item. The type and/or the preparation status of the food item may be determined based on the temperature identified by the temperature measuring device. In some embodiments, the temperature of the food item may be detected by a heat sensor.

Given the image of the food container, containing the food item, taken by the image capturing device and the predetermined structural properties of the food container, the food recognition device may identify the type of the food item placed in the one or more partitions of the food container. The food recognition device may comprise one or more processor and a memory. Further, the food recognition device may be in communication with the database via a network. The food recognition device may include one or more processors and various types of memory and storage devices that are typically found in a variety of user communication devices and user computing devices known in the art, related art, or developed later.

The system for determining a nutritional value of a food item, as described herein, may implement a server. The server may be implemented as any of a variety of computing devices, including, for example, a general purpose computing device, multiple networked servers (arranged in cluster or as a server farm), a mainframe, or so forth. The server may be installed, integrated, or operatively associated with the food recognition device, which may be configured to determine the nutritional value of the food item. The server may store various data in its database.

In one embodiment, the food recognition device may be implemented as a standalone and dedicated device including hardware and installed software, where the hardware is closely matched to the requirements and/or functionality of the software.

In another embodiment, the food recognition device may be installed on or integrated with a network appliance configured to establish the network among the components of the system. One or more of the food recognition device and the network appliance may be capable of operating as or providing an interface to assist exchange of software instructions and data among the food container, the weight sensor, the image capturing device, and the food recognition device. In some embodiments, the network appliance may be preconfigured or dynamically configured to include the food recognition device integrated with other devices.

In yet another embodiment, the food recognition device may be installed on or integrated with the server. For example, the food recognition device may be integrated with the server or any other computing device connected to the system's network. The server may include a module, which enables the server being introduced to the network appliance, thereby enabling the network appliance to invoke the food recognition device as a service. Examples of the network appliance include, but are not limited to, a DSL modem, a wireless access point, a router, a base station, and a gateway having a predetermined computing power and memory capacity sufficient for implementing the food recognition device.

In a further embodiment, the food recognition device may be installed on or integrated with one or more devices such as the image capturing device. The food recognition device may be any of the various computing devices equipped with an image capturing device capable of providing the functionality of the food recognition device. For example, a smartphone or a tablet with an integrated camera may be implemented in the system to perform the functionalities of the image capturing device and the food recognition device disclosed herein.

In a further embodiment, the food recognition device may be integrated with any number of devices in a distributed fashion such as being integrated with or installed on the image capturing device, the food container, and the food recognition device.

The food recognition device may be implemented in hardware or a suitable combination of hardware and software. In some embodiments, the food recognition device may be a hardware device including processor(s) executing machine readable program instructions for analyzing data, and interactions between the food container and the image capturing device. The "hardware" may comprise a combination of discrete components, an integrated circuit, an application-specific integrated circuit, a field programmable gate array, a digital signal processor, or other suitable hardware. The "software" may comprise one or more objects, agents, threads, lines of code, subroutines, separate software applications, two or more lines of code or other suitable software structures operating in one or more software applications or on one or more processors. The processor(s) may include, for example, microprocessors, microcomputers, microcontrollers, digital signal processors, central processing units, state machines, logic circuits, and/or any devices that manipulate signals based on operational instructions. Among other capabilities, the processor(s) may be configured to fetch and execute computer readable instructions in a memory associated with the food recognition device for performing tasks such as signal coding, data processing input/output processing, power control, and/or other functions. The food recognition device may include modules as software units executing on a processor.

In some embodiments, the food recognition device may include, in whole or in part, a software application working alone or in conjunction with one or more hardware resources. Such software applications may be executed by the processor(s) on different hardware platforms or emulated in a virtual environment. Aspects of the food recognition device may leverage known, related art, or later developed off-the-shelf software. Other embodiments may comprise the food recognition device being integrated or in communication with a mobile switching center, network gateway system, Internet access node, application server, IMS core, service node, or some other communication systems, including any combination thereof. In some embodiments, the food recognition device may be integrated with or implemented as a wearable device including, but not limited to, a fashion accessory (e.g., a wrist band, a ring, a watch, etc.), a utility device (a handheld baton, a pen, an umbrella, a watch, etc.), a body clothing, or any combination thereof.

The food recognition device may include one or more of a variety of known, related art, or later developed interface(s), including software interfaces (e.g., an application programming interface, a graphical user interface, etc.); hardware interfaces (e.g., cable connectors, a keyboard, a card reader, a barcode reader, a biometric scanner, a microphone, a camera, an interactive display screen, etc.); or both.

The system and method, described herein, may determine a nutritional value of the food item(s) placed in the food container. To begin the process of determining a nutritional value of the food item, the food recognition device may further employ computer vision techniques to recognize the image of the food container taken by the image capturing device. In its essence, the method for determining a nutritional value of the food item includes image acquisition, image rectification, image segmentation, food identification, and nutritional value determination.

The food recognition device may obtain the image of the food container containing the food item(s), hereinafter referred to as the instant image, from the image capturing device via the network. Additionally, the food recognition device may obtain the weight of the food item, measured by the weight sensor housed by the food container. Thereby, the instant image and its weight may be identified by the food recognition device.

The database, in communication with the food recognition device, may store information relating to the predetermined structural properties and visual properties (for example, colors) of the food container. In addition, the database may store a reference food container image as a model to be compared with the instant image obtained from the image capturing device. The user may take an image of the food container as the one or more partitions contains the food item, with the image capturing device. The reference food container image may be an image of the food container without any image distortions or color distortions therein. In some embodiments, the reference food container image may be taken from a top view, providing a two-dimensional image.

The instant image of the food container may be compared with the reference food container image, in order to rectify the instant image. As the user captures an image of the food container with various image capturing devices available, the image may contain image distortions or color distortions. The predetermined structural properties and visual properties of the food container may be compared with the instant image's structural and visual properties.

In one embodiment, the arrangements of the one or more partitions of the instant image may be compared to the reference food container image to correct the orientation of the food container in the instant image taken by the image capturing device. In some embodiments, the reference food container image may be directly compared pixel-to-pixel against the instant image to identify any image distortions. Knowing the predetermined structural properties of the food container, the image distortion of the instant image, if any, may be adjusted. In some embodiments, the boundary of the divider may be utilized to correct the orientation of the instant image of the food container. The boundary of the image may be compared with that of the reference food container image, in order to identify any image distortion (orientation distortion) that exists in the instant image of the food container taken by the image capturing device. For example, the one or more partitions may be arranged in a certain order. Given the known orientation of the one or more partitions from the reference food container image, the instant image of the food container may be rotated, thereby adjusting the orientation of the instant image. The divider, the peripheral wall, and the boundary of the food container may be utilized to correct such distortions in the food container's orientation in the instant image.

In some embodiments, the food container may be imprinted with a marking to indicate the correct orientation of the food container. The marking may be imprinted on the food container at a predetermined location, such that the instant image's orientation may be adjusted with reference to the marking's predetermined location. The marking may be any symbols, letters, or the like. The marking also may have a predetermined color in order to assist in the color adjustment of the instant image. The predetermined color of the marking may be used as a reference to adjust the color configuration of the instant image. In a preferred embodiment, the boundary of the food container may be utilized as the marking described herein.

The methods provided by the food recognition device may further comprise correcting the instant image of the food container into a canonical view. The canonical view may be set by the reference food container image. In order to identify the type of the food item placed in the one or more partitions, correcting image distortions in the instant image may be necessary. Examples of image distortions may include, but are not limited to, scale distortion, rotational distortion, projective distortion, and barrel distortion. The canonical view may be obtained by applying a transform to compensate for the image distortions. The transform may be a geometric transform.

In one embodiment, the transform may be identified by comparing a size and shape of the food container in the instant image to that of the reference food container image. The comparison may be made between the boundary identified from the instant image and the boundary identified from the reference food container image. As such, the transform may be identified by comparing the size and shape of the food container's boundary from the instant image and the reference food container image. The comparison may also be made between any structural properties of the food container in the instant image to the predetermined structural properties of the food container. By way of an example, resolutions of the images may be compared. Similarly, the resolutions of the images may be translated into an actual size, such as by identifying pixel-to-millimeters conversion. By way of another example, the size of the two images, the instant image and the reference food container image, may differ, due to varying distances between the image capturing unit and the food container at the moment of image capture. The size of the instant image may be adjusted by referencing the size of the food container in the reference food container image. Similarly, varying focal distances among the various types of image capturing device and the resulting images can be adjusted by identifying a predetermined size of the food container from the reference food container image.

In another embodiment, the transform may be identified by identifying at least two markings on the food container. The food container may have markings, patterns, or the like imprinted on the food container's surface which may be used as reference points. Two-dimensional coordinates of the markings may be identified within the instant image of the food container. The markings may be assigned with predetermined two-dimensional coordinates, such that the two-dimensional coordinates of the markings in the instant image can be compared with the predetermined two-dimensional coordinates to identify the transform. The instant image may be adjusted by identifying the differences in the locations of the two markings between the instant image and the reference food container image. The differences may be compensated by adjusting the instant image within the two-dimensional space. For example, the adjustment may be made according to the x-axis, the y-axis, the distance between the two markings, the angle between the two markings, and so on. Similarly, the locations of the markings in the instant image may be compared with that of the reference food container image to identify the transform that can correct any image distortions. Once compared, the instant image, if it has any distortions, may be adjusted by matching the two markings to that of the reference food container image.

In yet another embodiment, the food container may be imprinted with a single marking. The orientation of the single marking may be utilized to identify any three-dimensional rotational distortions, namely pitch, yaw, and roll in a Cartesian coordinate system. The database may include an image of the marking without any three-dimensional distortion to be provided as a model. Similarly, the boundary of the reference food container image may be utilized as a model having no three-dimensional distortion. The boundary of the reference food container image and the instant image may be compared to identify any three-dimensional distortions (rotation in any of the three-axis). If any three-dimensional distortion is identified, a transform may be calculated to compensate for such distortion. In this embodiment, the transform may represent the three-dimensional distortion in angles along the x-y-z axes in a three-dimensional Cartesian coordinate system and a distortion in size of the instant image, resulting from varying distances between the image capturing device and the food container. The transform may be applied to the instant image to remove any three-dimensional distortions.

Color configuration of the instant image of the food container may be adjusted based on the predetermined color of the food container. In one embodiment, the predetermined color of the boundary with an assigned RGB value may be compared with the color of the boundary in the instant image. If any differences are identified, the color configuration of the image may be adjusted. The color configuration may include color saturation, light variation, contrast, brightness, and the like. The color configuration of the instant image may be matched to the assigned RGB value of the predetermined color of the boundary.

In another embodiment, the predetermined color of the other surfaces of the food container may be utilized in a similar manner to correct any color distortion by adjusting the color configuration of the instant image taken by the image capturing device. Similar to above embodiment of utilizing the predetermined color of the boundary, the other surfaces of the food container may be assigned a RGB value of a predetermined color, which may be used as a reference to adjust the color configuration of the instant image to match that of the reference food container image.

In yet another embodiment, the predetermined color of the marking imprinted on the food container may be utilized in a similar manner to adjust the color configuration of the instant image taken by the image capturing device.

The instant image of the food container containing food item may be segmented based on the one or more partitions. The boundary of the food container may be used to isolate each of the one or more partitions of the food container. Further, the food item in the instant image may be isolated from the food container.

Background of the instant image may be eliminated. The instant image may include the food container containing the food item and the background which represents the surrounding environment of the food container. For example, the instant image may include the food container and a table on which the food container is placed. In some embodiments, the background in the instant image may be eliminated by analyzing color differences between the food container and the background. The color differences may be identified by analyzing the instant image pixel by pixel. In this embodiment, the predetermined color of the food container may be utilized to identify the pixel belonging to the food container and the pixel belonging to the background. In some embodiments, the background in the instant image may be eliminated based on the boundary. The color of the boundary may be dissimilar from the background, such that the boundary is graphically contrasting or apparent from the background in the instant image. As such, the background in the instant image can be removed by eliminating the portion of the instant image that represents the background, for example, the portion outside of the boundary within the instant image.

In some embodiments, the background in the instant image may be eliminated based on the predetermined structural properties of the boundary. The boundary may be one of the predetermined structural properties to be used as a reference. The predetermined structural properties of the food container may include any combination of the boundary's location, size, orientation, shape, and the like. The predetermined structural properties of the boundary can be utilized to identify the location and outline of the boundary within the instant image, thus removing the portion outside of the boundary within the instant image.

In some embodiments, the segmentation of the instant image may be performed by aligning the boundary of the reference food container image with the instant image of the food container. With the image distortion removed, the two images, the instant image, and the reference food container image, may be aligned to segment out the one or more partitions. In some embodiments, the boundary outlining the peripheral wall of the food container may be aligned to segment the one or more partitions collectively. In some embodiments, the boundary outlining the divider may be aligned to segment the one or more partitions individually. A template image containing the boundary outlining the peripheral wall of the food container may be stored by the database. Similarly, a template image containing the boundary outlining the divider may be stored by the database. These two templates may be aligned with the instant image selectively, individually, and/or collectively, in order to segment and isolate the one or more partitions.

The color within the food container of the instant image may be analyzed (for example, pixel by pixel), in order to identify and isolate the food item within the instant image of the food container. In some embodiments, each of the segmented one or more partitions of the instant image may be analyzed to identify and isolate the food item within each of the one or more partitions. Colors of each of the one or more partitions may be analyzed (for example, pixel by pixel), to isolate food item within the food container of the instant image. The pixels of the instant image that do not represent the food item may be eliminated, thereby the segmented one or more partitions may further be isolated to obtain images of just the food item. Similarly, in some embodiments, the food item within the instant image may be identified and isolated without the process of segmentation described above.

In one embodiment, the food recognition device may gather information regarding features of the food item from the rectified and segmented instant image to identify the type of the food item. The features of the food item may include visual elements, such as volume, texture, color, spectrum, shape, and the like. The features of the food item may also include non-visual elements, such as, temperature, chemical composition, and the like. Based on the information received from the instant image of the food item, the food recognition device may then identify the type of the food item retained by each of the one or more partitions. In some embodiments, the features of the food item identified from the instant image may be compared to the database to determine a matching food type. The database may store expected features that indicate a corresponding food item. The database may store various types of food items and their features. The food recognition device may be in communication with the database, where various types of food items may be linked to their corresponding features expected from each of the various types of food item. By way of an example, visual features such as color, shape, and texture of strawberries may be matched with that of the instant image's food item to identify that the food item in the instant image is a strawberry. In this example, visual features of the strawberry, such as red, triangular, and perforated, may indicate the type of the food item.

The corresponding features expected from each of the various types of food items may be stored in the database. This database may be built through a machine learning process. The features of the various types of food items may be collected by gathering the corresponding features from images of model food items. The model food items and their corresponding features may be tested to validate whether or not enough corresponding features have been collected per type of the model food items, in order to recognize the type of the food items based on the features of food items. The database further may be updated as the system identifies the type of food items each time the user utilizes the food container disclosed herein. In some embodiments, the corresponding features expected from each of the various types of food items may be collected and presented to the database prior to any usage of the system begins.

In another embodiment, the features extracted from the food items of the instant image may be compared to the features extracted from the food items of the reference segmented food images stored in the database. The database may contain the reference segmented food images which are images of food items (the model food items) without any color distortions, structural distortions, and/or visual distortions discussed above. Features may be extracted from the reference segmented food images per types of food items and stored in the database to be used as references for identifying the type of the food item in the instant image.

In yet another embodiment, the food recognition device may be in communication with the database where it stores images of food items to be used as references (for example, the reference segmented food images), which can be compared with the instant image to identify the type of the food item. For example, the instant image and the images of food items from the database may be compared pixel-to-pixel to identify the type of the food item in the instant image. The similarity between the instant image and the image of the food item from the database may be analyze to identify a match. A threshold value may be used when analyzing the similarity between the two images, such that when the similarity is higher than the threshold value, the food recognition device may identify them as a match.

The food item may be a mixture of various ingredients. In this embodiment, the type of the food item may be identified by individually identifying each of the various ingredients of the food item, as well as collectively identifying the overall features of the food item. The food recognition device may be in communication with the database which stores information that links various ingredients to a matching type of food item. By way of an example, a pasta dish often includes a variety of ingredients. By analyzing an image of the pasta dish which would include a variety of ingredients, the one or more processors may identify that the food item being retained by the food container is a pasta dish made with the variety of ingredients identified from the instant image, for example meatball and spaghetti.

In some embodiment, the additional cooking ingredients may be identified from various computer vision techniques as described above. The food recognition device may identify the additional cooking ingredients, such as oil and spices based on the extracted featured of the food item. The features and/or images of the additional cooking ingredients may be stored by the database. For example, the food container may hold a pasta dish as the food item which may be garnished with parsley. The food recognition device may identity the food item as the pasta dish, in addition the garnished parsley may be identified as the additional cooking ingredients. This feature of identifying the additional cooking ingredients can be crucial to those allergic to certain food groups.

In yet another embodiment, the information obtained by the food recognition device may be further processed to identify a preparation status of the food item. The ingredient of the food item once cooked may change its volume, texture, spectrum, chemical composition, color, shape, temperature, and the like. The preparation status of the food item may be determined based on the instant image and/or features extracted from its food item. By way of example, when food is cooked the color of the food tends to change. By recognizing the color of the food item from the instant image, the preparation status of the food item may be identified. The features and/or images that indicated preparation status of the various food items may be stored by the database.

Given the type of the food item recognized from the instant image of the food container and the weight of the food item measured by the weight sensor, the food recognition device may determine the nutritional value of the food item placed in the one or more partitions of the food container.

In one embodiment, the database may store nutritional value conversion information which may indicate nutritional value of the various types of food items per weight. As such, the nutritional value of a food item may be determined based on the weight and type of the food item of the instant image. The nutritional value may include, but not limited to, calories, vitamins, sodium content, fat content, carbohydrates, and the like.

In another embodiment, the food item may be a mixture of various ingredients. In this embodiment, the nutritional value of the food item may be determined based on the various ingredient's weights and types, either collectively or severally. In some embodiments, the food recognition device may be in communication with the database which stores the nutritional values of various types of mixed food items. Once the type of the food item that is made of the mixture of various ingredients is recognized, the nutritional value may be determined based on the type of the mixed food item and the weight.

In some embodiments, the ingredients of the mixture of various ingredients may be individually identified to determine the nutritional value of the food item.

In some embodiments, a spatial ratio of the ingredients in the mixture of various ingredients may be identified for determining the mixed food item's nutritional value. The spatial ratio indicates a composition of each of the various ingredients in the mixed food item. The database may store a spatial ratio-to-type information where various types of mixed food items may be assigned with a predetermined spatial ratio. Once the type of such mixed food item is recognized, the spatial ratio-to-type information may be utilized to find the spatial ratio of the ingredients, followed by determination of nutritional value of each of the ingredients. In some embodiments, the spatial ratio of the mixed food item may be identified by analyzing the instant image. The ingredients of the mixed food item may be individually recognized by analyzing the instant image. For example, the isolated food from the instant image may be analyzed pixel by pixel to determine the spatial ratio among the ingredients of the mixed food item.

The food recognition device may further determine a volume of the food item placed in the one or more partitions. Based on the type and the weight of the food item in the instant image, the volume may be estimated. The database may store type-to-density information which entails densities of the various food types. With the known weight and known density, the volume of the food item may be derived. The nutritional value of the food item may be determined based on the derived volume of the food item and its type. In some embodiments, the volume of the food item may be approximated by a surface area of the food item (for example, the number of pixels of the food item that occupies the instant image). In some embodiments, the volume of the food item may be identified based on two or more instant images of the same food container taken at varying angles. The volume may be approximated by triangulation of a three-dimensional volume of the food item based on the two or more instant images.

The food recognition device may further be in communication with a computerized user interface for the user to interact and control the operation of the food recognition device, the system, and its components. The computerized user interface may display any input and output derived from the components of the system. The data processed by the one or more processors of the food recognition device may be displayed by the computerized user interface.

In one embodiment, the computerized user interface may indicate the weight of the food item through a display. The weight measured by the weight sensor may be displayed.

In another embodiment, the computerized user interface may indicate the type of the food item determined by the food recognition device based on the information obtained from the food image of the instant image.

In yet another embodiment, the computerized user interface may indicate the preparation status of the food item determined by the food recognition device based on the information obtained from the food image of the instant image.

In a further embodiment, the computerized user interface may indicate a nutritional value of the food item. The food recognition device may determine the nutritional value of the food item based on the information obtained from the weight sensor and the instant image. The nutritional value may further be determined by the food recognition device based on the preparation status identified by the food recognition device.

The computerized user interface may be configured to receive an input from the user. The computerized user interface may receive inputs from the user regarding their dietary requirements, such as a health condition, food allergy information, and the like. The input received from the user may further be communicated to the food recognition device to further evaluate and monitor the nutritional value of the food item and the eating habit of the user. The eating habit may include the speed in which the user consumes the food item, the frequency in which the user consumes a certain category of food, the amount of the food items the user consumes in each intake or during the meal, and the like. The eating habit may be monitored to identify any eating pattern and behavior. The food recognition device may provide a recommended meal plan suitable to the user based on the user input. The user input may be in any form including, but not limited to, text input, audible input, and the like. The recommended meal plan may be modified based on the user's medical condition which may be received by the food recognition device from the user or from an external device in communication with the food recognition device.

The user may also provide information about any food items consumed without using the food container through the computerized user interface. The user may manually input calories or any other nutritional information using the computerized user interface.

Turning now to FIG. 1, FIG. 1 illustrates an exemplary embodiment of the food recognition device and the food container in use. In this embodiment 100, the image capturing device may be integrated with the food recognition device 101. The food recognition device 101 may be positioned to take an image (the instant image) of the food container 109 containing three different types of food items 105, 106, and 107. The food container 109 may have three partitions 102, 103, and 104 formed therein. The three partitions 102, 103, and 104, may be compartmentalized by the peripheral wall of the food container 109 and the dividers 108. The divider 108 and the periphery of the food container (the boundary) may be outlined with the predetermined color. In this embodiment, the food recognition device 101 may be a smartphone or other similar types of portable computing devices which comprises one or more processors and a memory to execute the food recognition method described herein.

Figure 2:
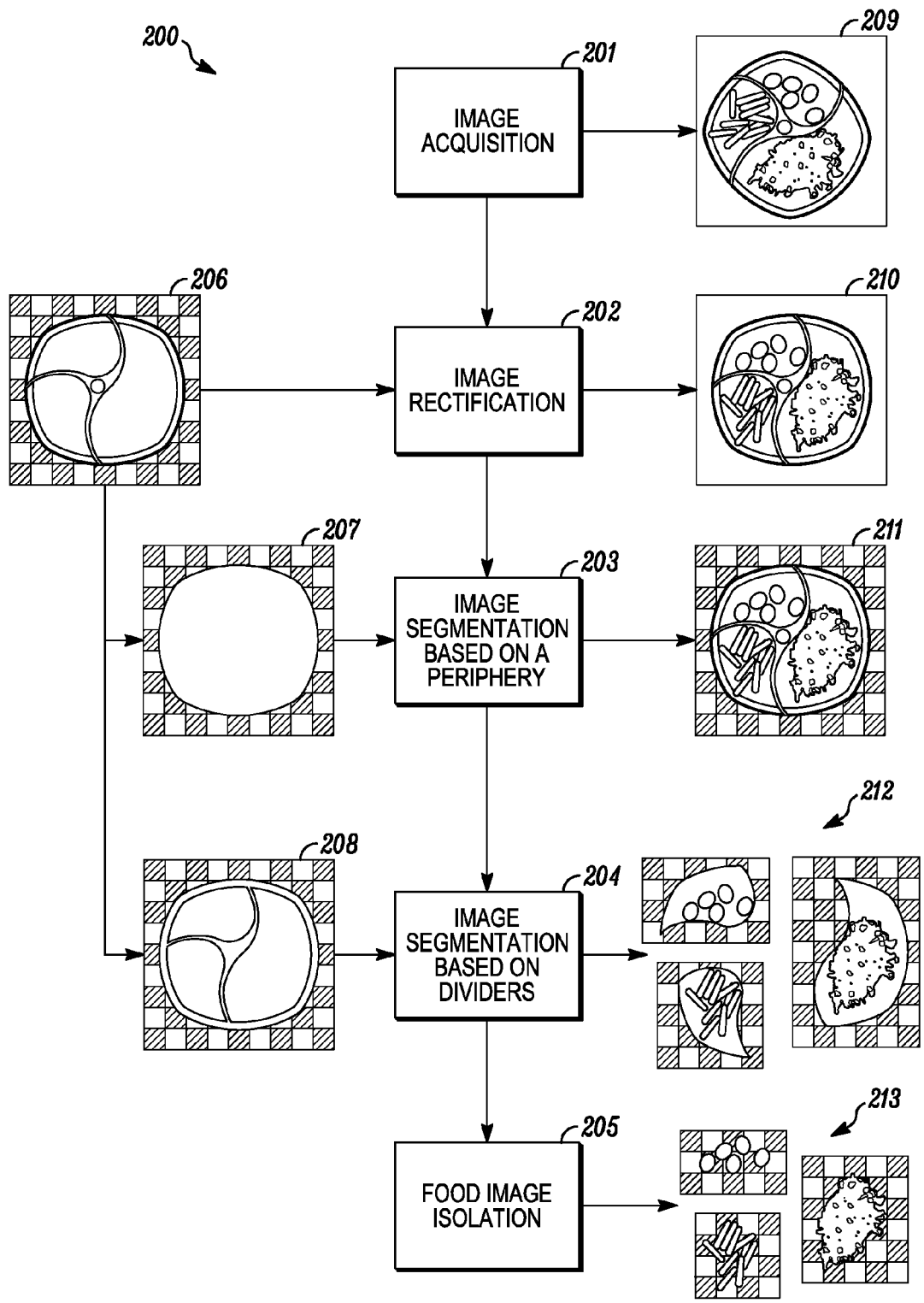
FIG. 2 provides an exemplary embodiment of the computer vision technique methods for food image isolation.

FIG. 2 shows an exemplary embodiment of the computer vision technique method for food image isolation. In this embodiment 200, the process may begin with an image acquisition 201. In the image acquisition 201 step, the instant image 209 of the food container captured by the image capturing device may be obtained by the food recognition device. The database may store the reference food container image 206. The reference food container image 206 may have no background therein. The database may further include the outline of the peripheral wall 207 of the food container within the reference food container image 206. The outline of the peripheral wall 207, also may be referred to as the first template 207, may define the food container's outermost margin. Further, the database may include a second template 208 outlining the boundary of the three partitions of the food container.

In the image rectification step 202, the reference food container image 206 may be compared with the instant image 209 to rectify the instant image 209. The rectified instant image 210 is the result of the image rectification step 202, which contains no image distortions. In this embodiment, the orientation of the instant image 209 is rectified to match the arrangement of the one or more partitions to that of the reference food container image 206. The predetermined color of the boundary and/or the food container may be utilized here to adjust the color configuration of the instant image 209. In the step of image segmentation based on a periphery 203, the background of the instant image may be eliminated, by aligning the first template 207 with the rectified instant image 210. The image 211 represents the rectified instant image 210 without any background.

Once the background is removed, the second template 208 may be aligned with the image 211 (without any background) for the step of image segmentation based on dividers 204. The second template 208 provides the outline of the dividers of the food container. As a result, each of the three partitions of the instant image 209 may be segmented 212. In the step of food image isolation 205, once the three partitions are segmented as shown in 212, the food items of the instant image 209 may be isolated by eliminating the other surfaces of the food container 213. This may be done by eliminating the pixels of the segmented image 212 based on the predetermined color of the other surfaces of the food container.

Figure 3:
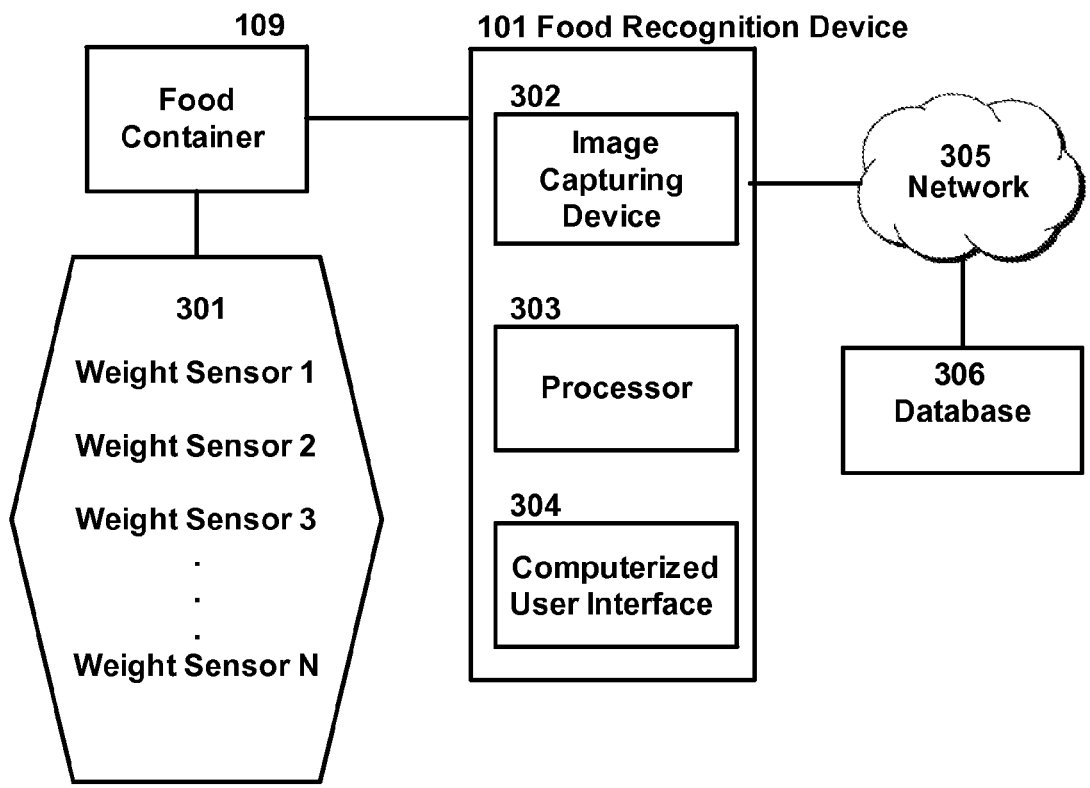
FIG. 3 provides an exemplary embodiment of the system for determining a nutritional value of a food item.

FIG. 3 illustrates an exemplary embodiment of the system for determining a nutritional value of a food item. The system may comprise the food container 109, embedded with a plurality of weight sensors 301. Each of the plurality of the weight sensors may be respectively positioned to measure the weight of the food items retained by the one or more partitions of the food container 109. The system may further comprise the food recognition device 101. In this embodiment, the food recognition device 101 is shown as an integrated device which comprises the image capturing device 302 installed thereon. The food recognition device may further comprise a processor 303 and a computerized user interface 304. The food recognition device 101 may be in communication with the database 306 via the network 305.

Figure 4:
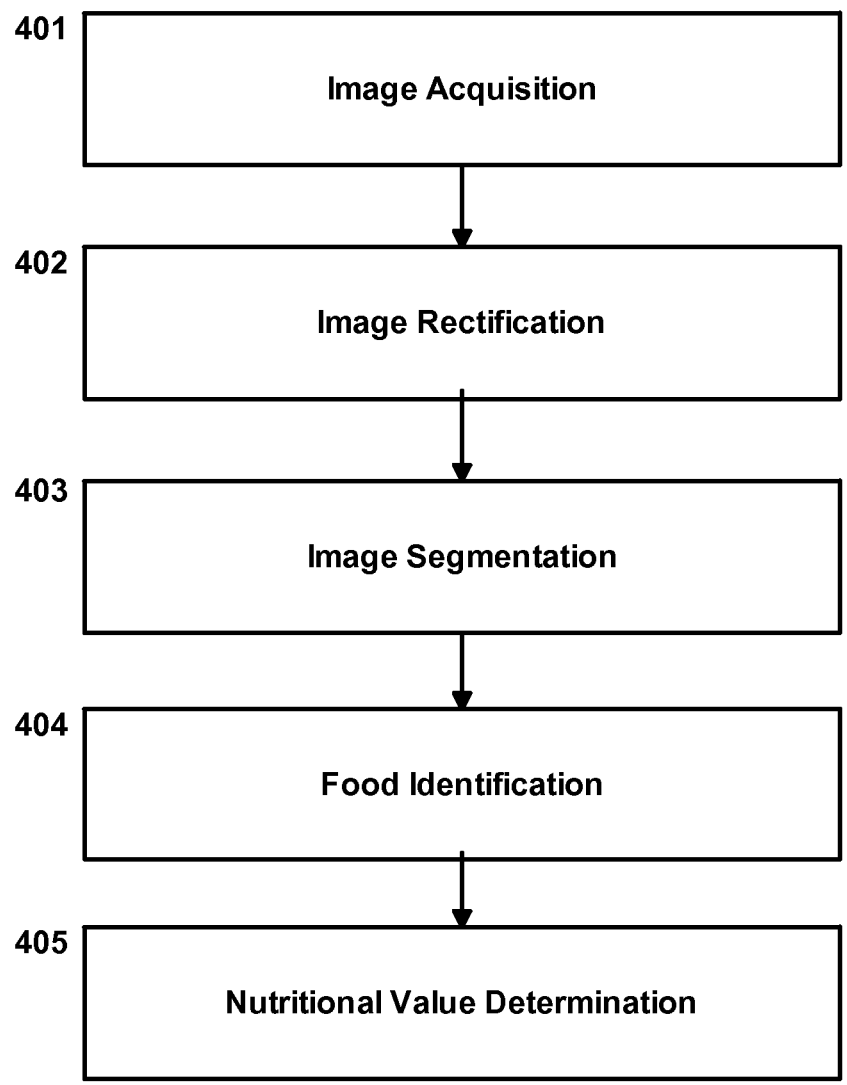
FIG. 4 provides a flowchart of an exemplary embodiment of the computer vision techniques of the present disclosure.

FIG. 4 provides a flowchart of an exemplary embodiment of the computer vision techniques of the present disclosure. The image captured by the image capturing device (the instant image) is acquired by the food recognition device at 401. At step 402, the food recognition device may rectify the instant image based on the reference food container image. The rectified instant image may further be segmented based on the boundary at step 403. At step 404, the food item within the instant image may be isolated and its type may be identified. Knowing the type of the food item and the weight of the food item, at step 405, the nutritional value of the food item retained by the food container may be determined.

Figure 5:
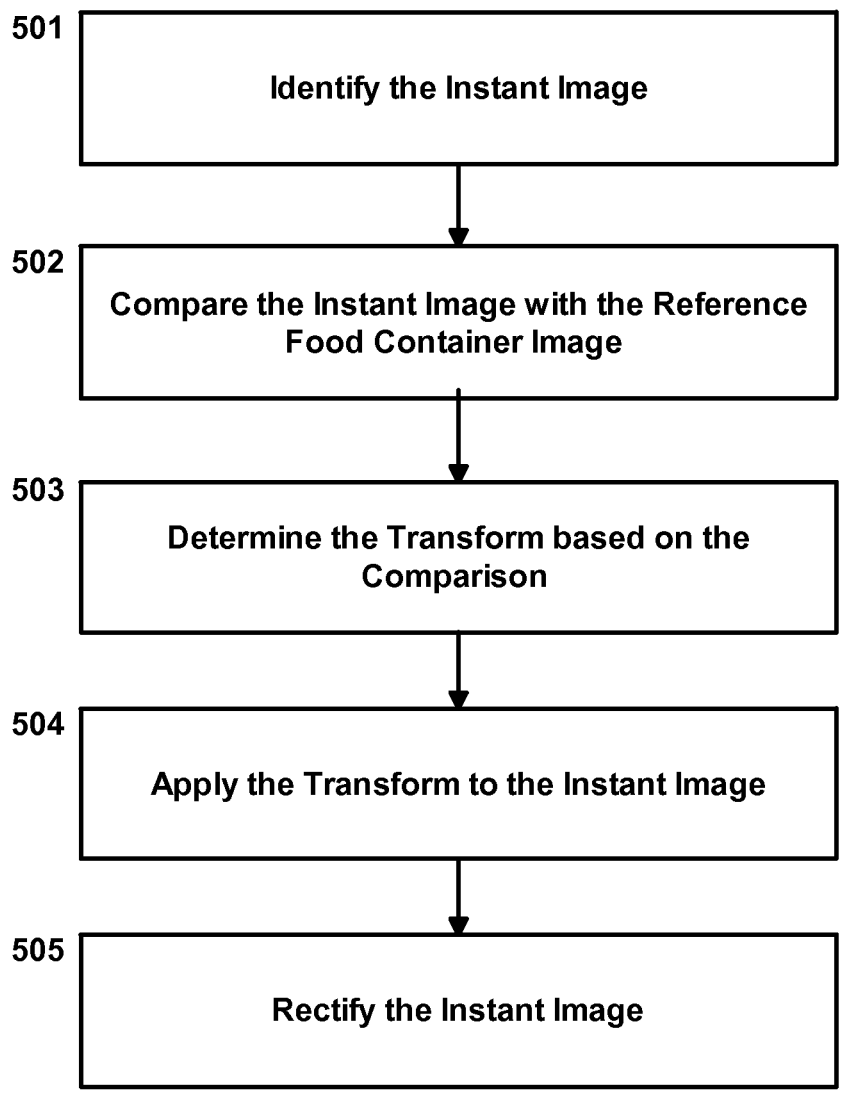
FIG. 5 provides a flowchart of the image rectification process.

FIG. 5 provides a flowchart of the image rectification process according to the present disclosure. To begin the image rectification process, the instant image may be identified 501. The instant image may be compared with the reference food container image, at 502, to identify any image distortions that may exist in the instant image. The transform may be determined by the food recognition device based on the comparison 503 between the instant image and the reference food container image. At step 504, the transform may be applied to the instant image, then the instant image may be rectified 505.

Figure 6A:
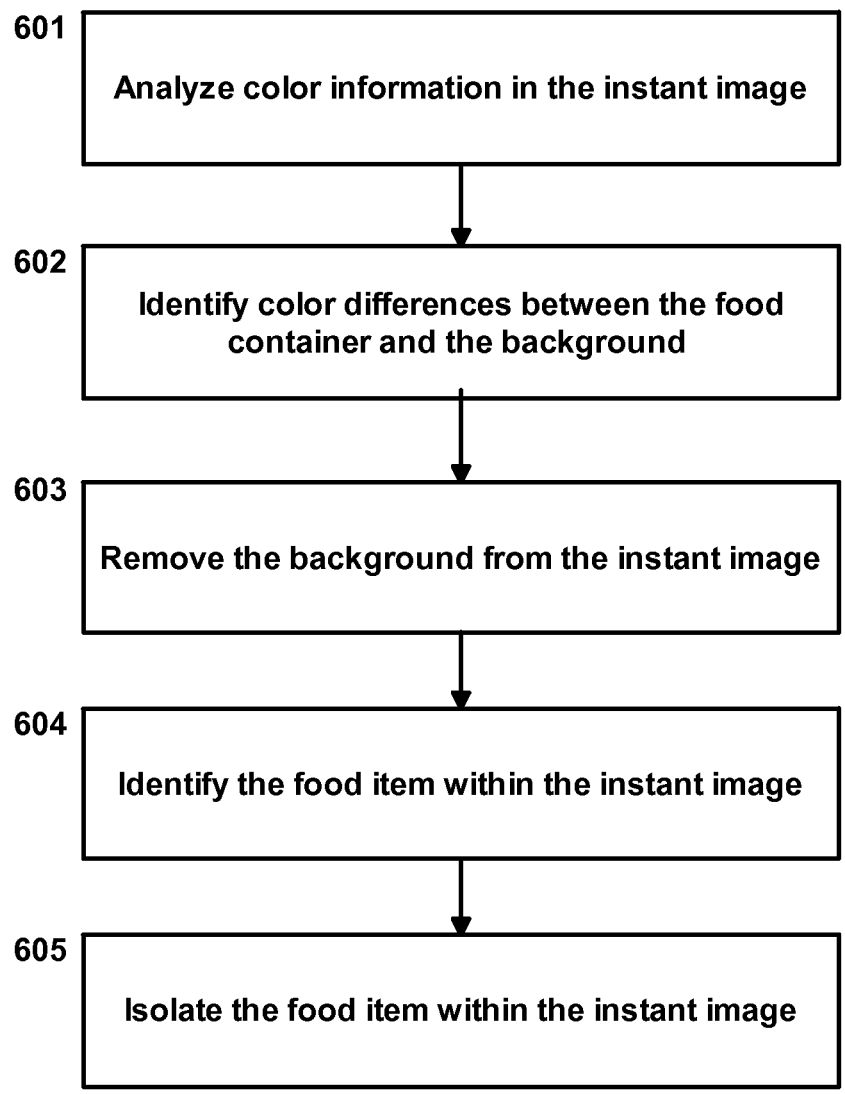
FIG. 6A provides an exemplary embodiment of the food item isolation process.
Figure 6B:
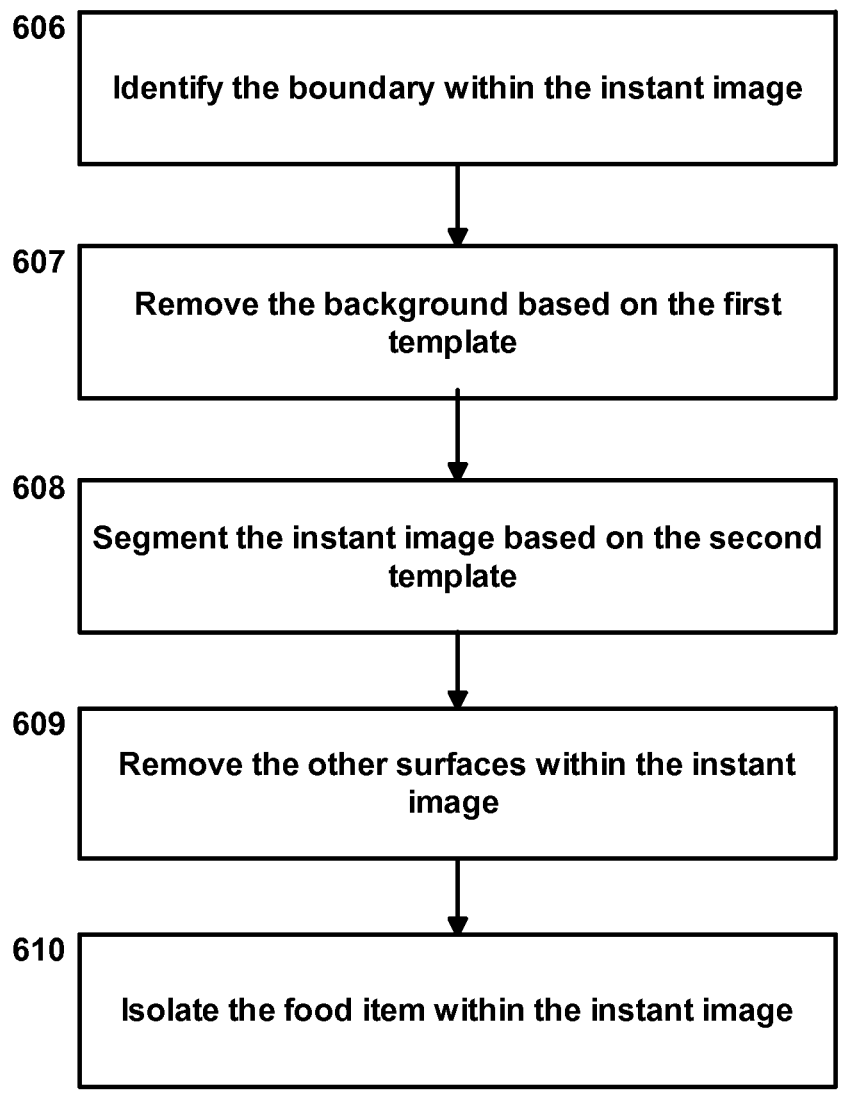
FIG. 6B provides another exemplary embodiment of the food item isolation process.

FIG. 6A and FIG. 6B describe exemplary embodiments of the food item isolation process of the present disclosure. The food item isolation process may be carried out by the food recognition device. In FIG. 6A, the process begins with analyzing the color information in the instant image 601. The color difference between the food container and the background may be identified from the instant image 602. Based on the identified color difference between food container and the background in the instant image, the background of the instant image may be removed 603. At step 604, the food item within the instant image, with the background removed, may be identified based on the predetermined color of the other surfaces of the food container. Finally, the food item within the instant image may be isolated 605, by removing the other surface represented in the instant image.

In FIG. 6B, the boundary within the instant image may be identified by the food recognition device at 606. The boundary may comprise the first template and the second template, which respectively represents the peripheral wall and the divider of the food container. Based on the first template, the background may be removed 607. This may be done by aligning the first template with the instant image. At step 608, the one or more partitions of the food container in the instant image may be segmented based on the second template. Once segmented, at 609, the other surfaces within the instant image may be removed, thereby isolating the food item within the instant image 610.

Figure 7A:
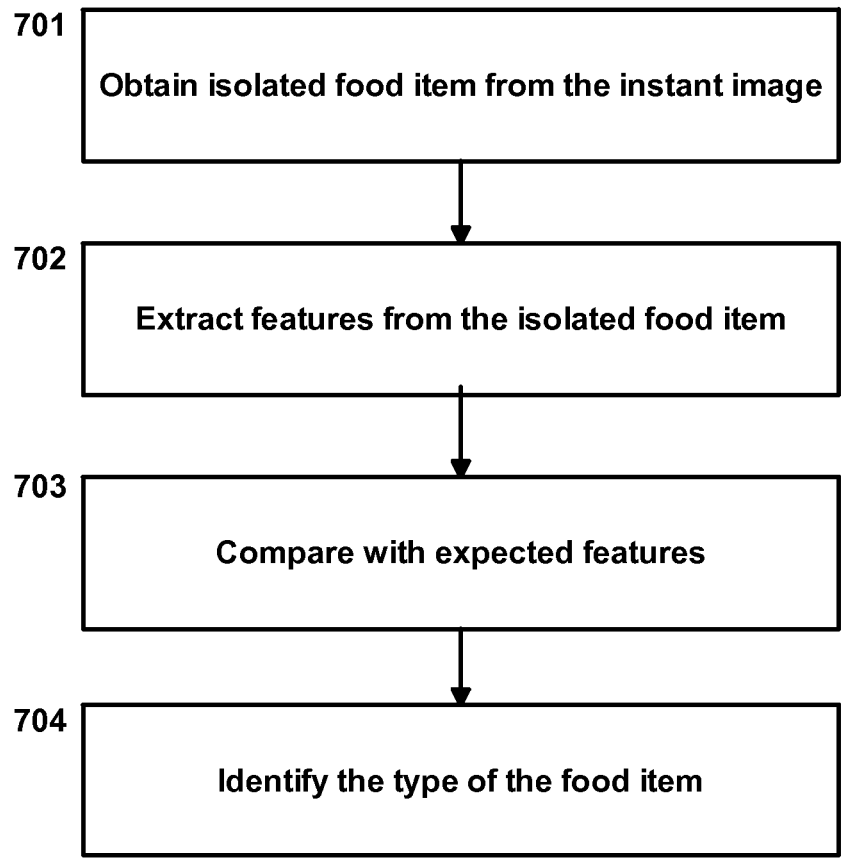
FIG. 7A provides an exemplary embodiment of the food identification process.
Figure 7B:
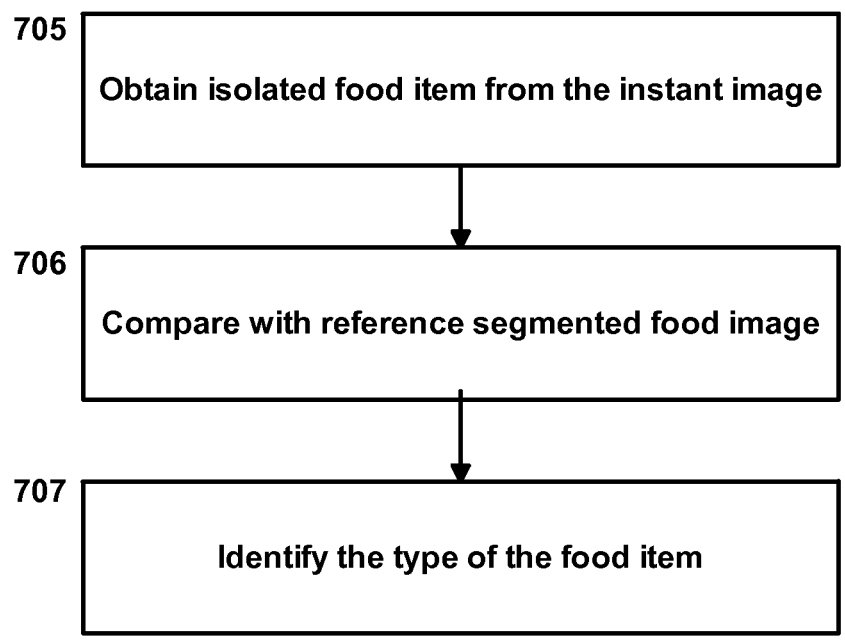
FIG. 7B provides another exemplary embodiment of the food identification process.

FIG. 7A and FIG. 7B illustrate exemplary embodiments of the food identification process in flow charts. FIG. 7A describes the food identification process where the features of the food image in the instant image is compared with the expected features corresponding to the various types of food items stored in the database. The database may store the various types of food items, each linked to various features corresponding to each of the various types of food items. At step 701 and 705, the food recognition device may obtain the isolated food item of the instant image. In FIG. 7A, the features of the isolated food item may be extracted 702, and compared with the expected features 703. In FIG. 7B, the isolated food item of the instant image may be compared with the reference segmented food images 706 stored in the database. The reference segmented food images are model food item images that represent the various types of food items. The isolated food item and the model food images may be compared to determine the similarity between the two, in order to identify whether the isolated food item matches closely to the one of the model food images (the reference segmented food images). The step 706 may further involve extraction of features from the model food images which may be compared with the features extracted directly from the instant image. In a preferred embodiment, the features may include texture and color of the food item. At steps 704 and 707, the type of the food item in the instant image is identified.

Figure 8:
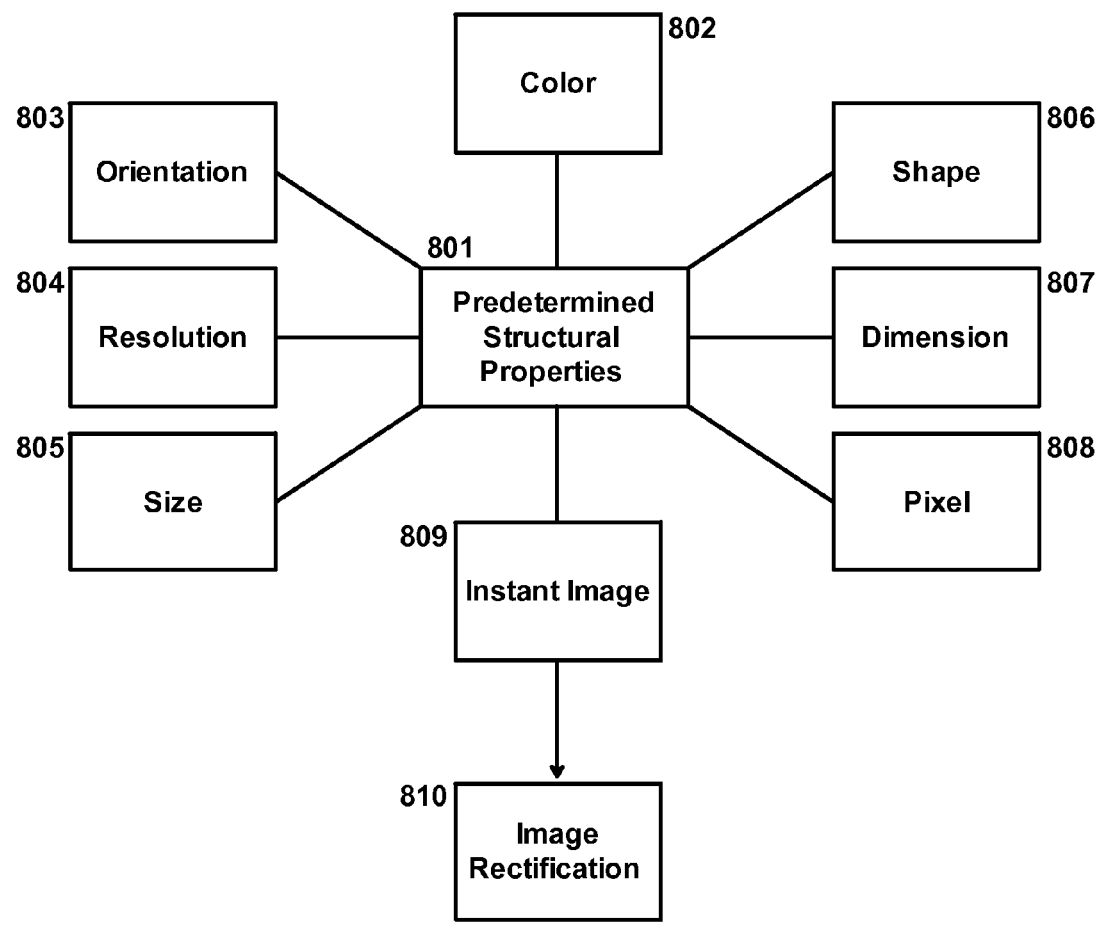
FIG. 8 provides a schematic diagram of the predetermined structural properties which may be referenced to rectify the instant image.

FIG. 8 illustrates a schematic diagram of the predetermined structural properties which may be referenced to rectify the instant image. The instant image 809 may be compared against the predetermined structural properties 801 of the food container for image rectification 810. The predetermined structural properties 801 may include the color 802 (the color of the boundary, the other surfaces, and/or any other portions of the food container), the orientation 803, the resolution 804, the size 805, the shape 806, the dimension 807, and the pixel 808. The orientation 803 may be referenced to adjust the rotational distortion that may exist in the instant image. The resolution 804, the size 805, the shape 806, and the dimension 807 may be referenced to adjust affine transformation, scale distortion, and/or projective distortion, which may exist in the instant image. The pixel 808 may be referenced to adjust the sizing of the instant image, where the pixel can be converted to a unit of measurements, such as millimeters. Lastly, the color 802 may be referenced to adjust the color configuration of the instant image. These and any other predetermined structural properties of the food container may be severally or collectively utilized to rectify the instant image.

Figure 9:
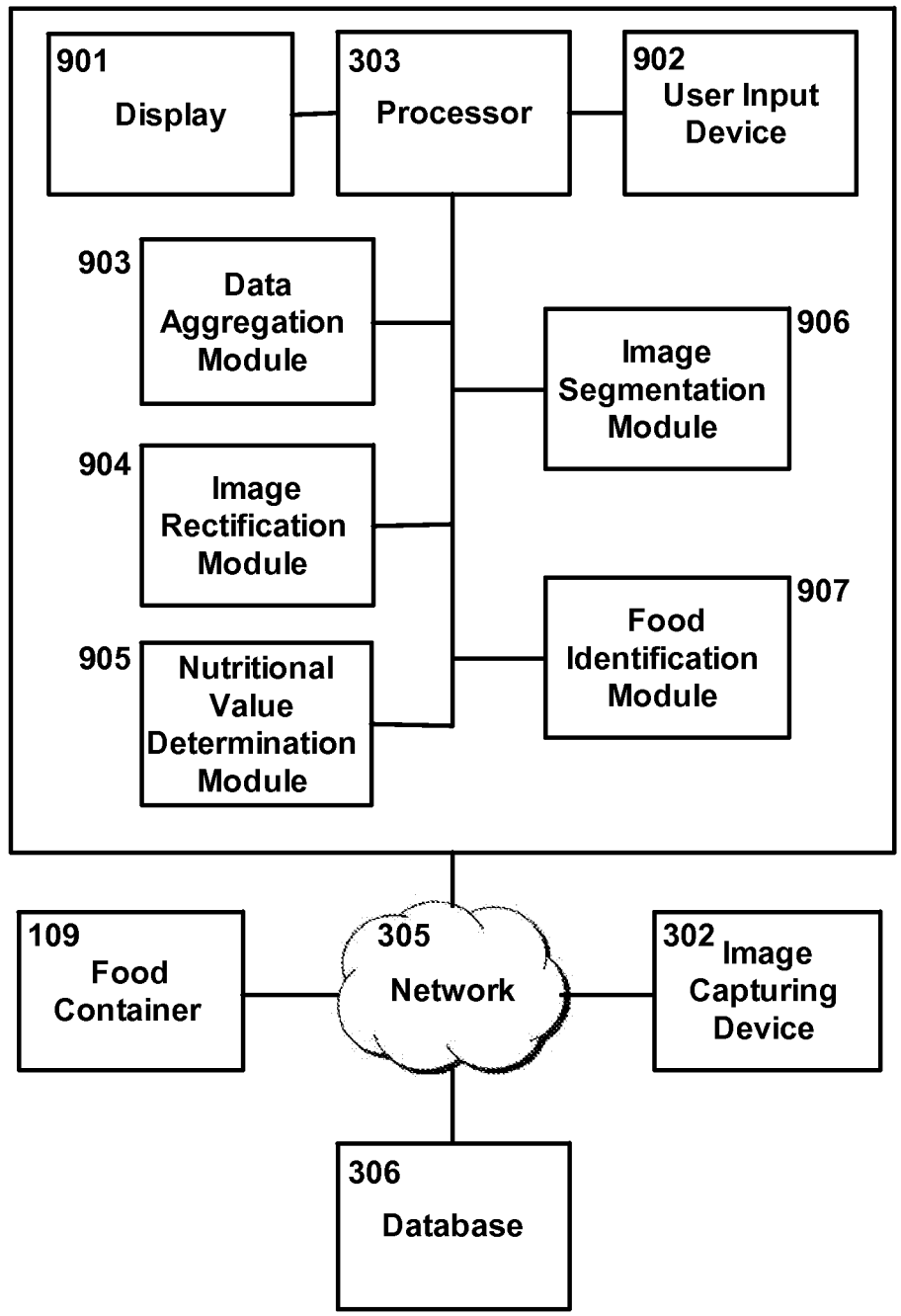
FIG. 9 provides an exemplary embodiment of the system for determining the nutritional value of a food item implementing the food recognition device as a standalone device.

FIG. 9 provides an exemplary embodiment of the system for determining the nutritional value of a food item, where the food recognition device is implemented as a standalone device. The system may comprise the food recognition device 101, the food container 109, the image capturing device 302, and the database 306, where the components of the system may be in communication with one another via the network 305. The food recognition device 101 may comprise a display 901, the processor 303, and the user input device 902. The food recognition device 101 may further comprise various modules executing on the processor 303. The various modules may comprise the data aggregation module 903, the image rectification module 904, the image segmentation module 906, the food identification module 907, and the nutritional value determination module 905. The data aggregation module 903 may be responsible for obtaining the weight from the weight sensor and the instant image from the image capturing device 302. The image rectification module 904 may perform the process and method for rectifying the instant image according to the present disclosure. The image segmentation module 906 may provide the process and method for segmenting the instant image as described herein. The food identification module 907 may be responsible for isolating the food item within the instant image and identifying the type of the food item. Finally, the nutritional value determination module 905 may perform the process and method for determining the nutritional value of the food item according to the present disclosure.

While several variations of the present invention have been illustrated by way of example in preferred or particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

Those skilled in the art will readily observe that numerous modifications, applications and alterations of the device and method may be made while retaining the teachings of the present invention.

What is claimed is:

1. A system using a food recognition device in communication with a database via a network, that determines a nutritional value of a food item, comprising:
- a food container with one or more partitions, the one or more partitions being defined by a boundary outlined by a divider and a peripheral wall formed by the food container, wherein the food container receives the food item, the food container being characterized by a predetermined structural properties;
- a weight sensor being placed within the food container, positioned to measure a weight of the food item being received by each of the one or more partitions;
- an image capturing device capturing an image of the food container; and
- the food recognition device, with a processor and a memory, in communication with the weight sensor and the image capturing device, configured to:
  - obtain the image of the food container from the image capturing device;
  - correct orientation of the image by aligning the boundary in the image with the boundary in a reference food container image stored in the database;
  - segment the image based on the boundary to isolate each of the one or more partitions; and
  - identify a type of the food item by comparing each segmented image to a reference segmented food image stored in the database.

2. The system of claim 1 wherein the step of correcting orientation of the image comprises correcting the image to a canonical view, wherein the canonical view is obtained by applying a transform to compensate for an image distortion of the image, the image distortion being identified based on the predetermined structural properties of the food container.

3. The system of claim 2 wherein the transform is determined by:
- identifying at least two markings in the image of the food container;
- determining two-dimensional coordinates of each of the at least two markings with respect to the reference food container image; and
- determining the transform to compensate for the image distortion in the image by comparing the two-dimensional coordinates between the image and the reference food container image.

4. The system of claim 1 wherein the food recognition device is further configured to adjust color of the image based on a predetermined color of the boundary, the boundary having the predetermined color dissimilar from other surfaces of the food container.

5. The system of claim 1 wherein the food recognition device is integrated with the image capturing device.

6. The system of claim 1 wherein the food recognition device is further configured to:
- remove background in the image based on the boundary of the food container; and
- isolate the food item, within the image, based on difference in color between the food item and other surfaces of the food container.

7. The system of claim 6 wherein the step of isolating the food item comprises analyzing the image, pixel by pixel, to eliminate pixels of the image that do not represent the food item.

8. The system of claim 1 wherein the step of identifying the type of the food item comprises comparing features of the food item from the image to features of the reference segmented food image, the features comprising color and texture that indicates types of food items.

9. The system of claim 1 wherein the food recognition device is further configured to determine the nutritional value of the food item based on the weight and the type of the food item.

10. The system of claim 9 wherein the food recognition device determines the nutritional value of the food item further based on a spatial ratio among ingredients of the food item in the image, the nutritional value of each of the ingredients being determined separately, and the spatial ratio being identified based on at least one of:
- a spatial ratio-to-type stored by the database; and
- individually identifying each of the ingredients and their composition in the food item.

11. The system of claim 1 wherein the food recognition device is further configured to determine the nutritional value of the food item based on a volume of the food item, the volume being determined by identifying a density of the food item from a type-to-density list stored in the database and the weight.

12. A method to use a system using a food recognition device in communication with a database via a network, that determines a nutritional value of a food item, comprising:
- capturing, with an image capturing device, an image of a food container, wherein the food container has one or more partitions, the one or more partitions being defined by a boundary outlined by a divider and a peripheral wall formed by the food container, wherein the food container receives the food item, the food container being characterized by a predetermined structural properties;
- obtaining, with a food recognition device, the image of the food container from the image capturing device, the image capturing device being in communication with the food recognition device;
- obtaining, with the food recognition device, a weight of the food item from a weight sensor, the weight sensor being positioned to measure the weight of the food item being received by each of the one or more partitions, wherein the weight sensor is in communication with the food recognition device;
- correcting, with the food recognition device, orientation of the image by aligning the boundary in the image with the boundary in a reference food container image stored in the database;
- segmenting, with the food recognition device, the image based on the boundary to isolate each of the one or more partitions; and
- identifying, with the food recognition device, a type of the food item by comparing each segmented image to a reference segmented food image stored in the database.

13. The method of claim 12 wherein the step of correcting orientation of the image comprises correcting the image to a canonical view, wherein the canonical view is obtained by applying a transform to compensate for an image distortion of the image, the image distortion being identified based on the predetermined structural properties of the food container.

14. The method of claim 13 wherein the transform is determined by:
- identifying at least two markings in the image of the food container;
- determining two-dimensional coordinates of each of the at least two markings with respect to the reference food container image; and
- determining the transform to compensate for the image distortion in the image by comparing the two-dimensional coordinates between the image and the reference food container image.

15. The method of claim 12 further comprising the step of adjusting, with the food recognition device, color of the image based on a predetermined color of the boundary, the boundary having the predetermined color dissimilar from other surfaces of the food container.

16. The method of claim 12 further comprising the steps of:
- removing, with the food recognition device, background in the image based on the boundary of the food container; and
- isolating, with the food recognition device, the food item within the image, based on difference in color between the food item and other surfaces of the food container.

17. The method of claim 12 wherein the step of identifying the type of the food item comprises comparing features of the food item from the image to features of the reference segmented food image, the features comprising color and texture that indicates types of food items.

18. The method of claim 12 further comprising the step of determining the nutritional value of the food item, with the food recognition device, based on the weight and the type of the food item.

19. The method of claim 18 wherein the nutritional value of the food item is determined further based on a spatial ratio among ingredients of the food item in the image, the nutritional value of each of the ingredients being determined separately, and the spatial ratio being identified based on at least one of:
- a spatial ratio-to-type stored by the database; and
- individually identifying each of the ingredients and their composition in the food item.

20. The method of claim 12 further comprising the step of determining the nutritional value of the food item, with the food recognition device, based on a volume of the food item, the volume being determined by identifying a density of the food item from a type-to-density list stored in the database and the weight.

* * * * *